Aug. 23, 1955 R. S. MOORE Plant Pat. 1,412

ROSE PLANT

Filed Sept. 13, 1954

WITNESS

Addison E. Avery

INVENTOR

Ralph S. Moore

Webster & Webster

ATTYS.

United States Patent Office

Plant Pat. 1,412
Patented Aug. 23, 1955

1,412

ROSE PLANT

Ralph S. Moore, Visalia, Calif.

Application September 13, 1954, Serial No. 455,808

1 Claim. (Cl. 47—61)

The present invention relates to a new and distinct variety of miniature rose plant whose major novel characteristic is full double flowers whose petals are substantially pure or snow white in color; the petals being a cleaner or more intense white than those of any known variety of white-flowering miniature rose variety, as for example Pixey (United States Plant Patent No. 408), and Cinderella (United States Plant Patent No. 1,051).

Another unique characteristic of the instant variety of rose plant is that the substantially pure white petals of the flowers do not tend to turn to shades of pink with age or cool weather, which is true of the Pixey and Cinderella miniature rose varieties.

An additional characteristic of the present variety of miniature rose plant is the presence of green styles which give the visual effect of a green dot in the center of the otherwise pure white flower.

Still another distinguishing characteristic of the present variety of miniature rose plant is its bushy, much branched, growing habit, tending to spread in growth to a width greater than height; the variety thus being an ideal border, lawn edge, or ground cover plant, as well as an excellent dwarf pot plant.

A still further characteristic of the variety is that the full double flowers bloom abundantly, and have a sweet honeysuckle fragrance.

The variety is also characterized by being seedless and substantially thornless.

The herein claimed variety of miniature rose plant was originated in my nursery at Visalia, California; the variety being an F–2 seedling of *Rosa wichuraiana* × an unamed seedling; both parent varieties being unpatented. The present variety is believed to be the first miniature rose plant with the species *Rosa wichuraiana* in its ancestry.

Subsequent to origination of the variety it was successfully reproduced in such nursery by both cuttings and budding; the reproductions having been found to carry forward all of the characteristics of the seedling parent.

Figure 3:
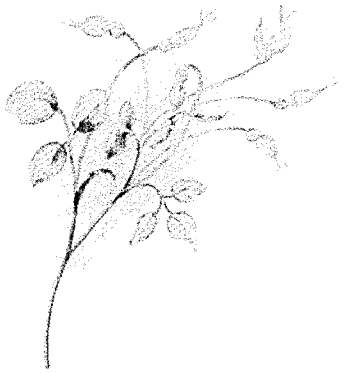
Fig. 3 is a similar view, but shows one of the buds partially opened.
Figure 1:
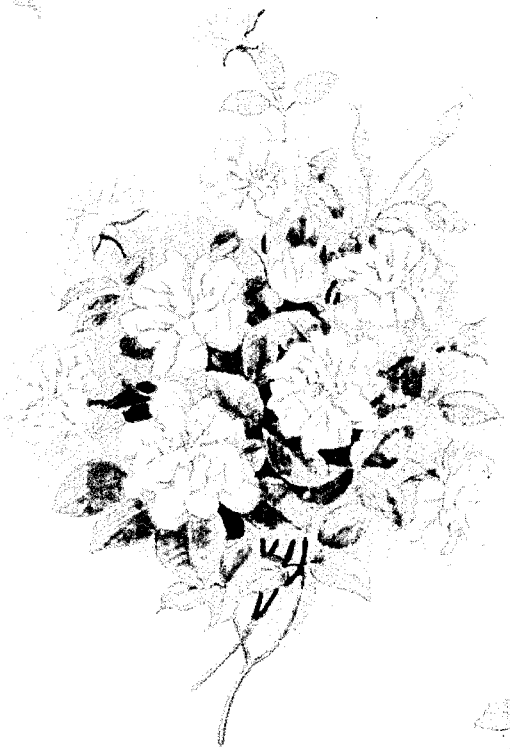
Fig. 1 is an elevation showing a number of flowers and buds of the variety, together with leaves and twigs.
Figure 2:
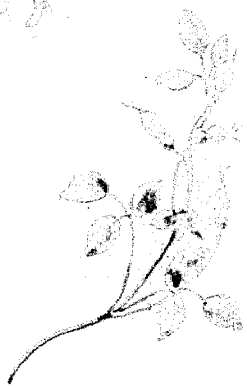
Fig. 2 is an elevation showing a sprig of the foliage with unopened buds.

Referring now specifically to the new and distinct variety of rose plant, the following is a detailed description thereof in outline; all major color plate identifications being to Maerz and Paul Dictionary of Color.

Type: Dwarf; bushy; hardy; garden decoration; greenhouse, pot plant.

Class: Wichuraiana—miniature.

Flowers:

*Continuity.*—Continuous.

*Fragrance.*—Moderate, sweet honeysuckle.

Flowers borne: From two to fifteen on a normal stem.

Quantity of bloom: Abundant both outdoors and in green house.

Bud:

*Peduncle.*—Medium length; medium strong; erect.

*Color.*—Reddish (13–A–8) with numerous brown hairs.

*Before calyx breaks.*—

Size—Small.

Form—Pointed; oval, without foliaceous appendages on the surface of the bud, with foliaceous parts extending beyond the tip of the bud equal to one-quarter to one-half of its length.

Color—Medium green (21–J–6).

*As calyx breaks.*—

Color—White with pink (1–F–7) tint.

*As first petal opens.*—

Size—Small.

Form—Short; ovoid.

Color (both outside and inside)—White with pink (1–F–7) tint, with a small amount of yellow at the base.

Bloom:

*Size.*—When fully opened—small, averaging 1⅛″ to 1⅜″ in diameter.

*Petalage.*—Very double, with from forty to fifty petals arranged irregularly.

*Form.*—At first flat cupped; becoming at maturity very loosely rolled outwardly.

Petals: Thin; satiny both inside and outside.

*Shape.*—Outside—obovate; intermediate—obovate; inside—obovate to narrow or spatulate.

*Color.*—Both surfaces pure white (1–A–1) without color shading; newly opened flower—clean frosty white; three days open—clean frosty white without any tendency to shade to pink even in cool weather.

*Behavior.*—Persist.

*Flower longevity.*—Bush in garden—three to five days in mid-summer; cut roses, grown in greenhouse, kept at living room temperature—two to three days in April–May.

Reproductive organs:

*Stamens.*—None.

*Pollen.*—None.

*Pistils.*—Few; imperfect.

*Styles.*—Uneven; short; green; the green styles give the effect of a tiny green dot (17–G–3) in the center of the opened white flower.

*Stigma.*—None.

*Apex.*—None.

*Seeds.*—None.

Plant:

*Foliage.*—

Leaves—Heavy; gloss; compound of five; moderately small; abundance—normal.

Leaflets — Ovoid; apex—acute; base—round; margin—serrate.

Color—Upper surface—medium green (22–L–8); under surface (21–K–7).

Rachis—Upper side—smooth; under side—sparsely thorny.

Stipules—Short; narrow, with short points turning out at an angle of more than 45°.

Growth:

*Habit.*—Dwarf; bushy; much branched; tendency to spread—growing wider than tall.

*Growth.*—Vigorous.

*Canes.*—Medium.

*Main stems.*—

Color—Green.

Thorns—Few-hooked downward, with short narrow base.
Prickles—None.
Hairs—None.

*Branches.*—
Color—Green.
Thorns—Few.
Prickles—None.
Hairs—None.

*New shoots.*—
Color—Green, sometimes tinted slightly with bronze or red.
Thorns—Very few, hooked downward.
Prickles—None.
Hairs—None.

As compared to the Pixie and Cinderella varieties of miniature rose plant, the present variety is not as dwarf and thorny as the Pixie and has larger flowers, and as compared to the Cinderella has larger flowers, larger foliage, and more bushy growth; the petals of the flowers of the instant variety being a more intense white without the tendency of said petals to shade to pink with age and in cool weather.

The miniature rose plant and its flowers as herein described may vary in slight detail due to climatic and soil conditions under which the variety may be grown.

Having thus described my invention I claim:

A new and distinct variety of miniature rose plant, substantially as described and illustrated, characterized by small but full double flowers of honeysuckle fragrance whose petals are pure white and persist in true color, and by green styles defining a tiny green dot in the center of the opened flower; the plant growth being bushy, much branched, and tending to spread to a width greater than the height; propagating easily from cuttings; blooming abundantly and continuously; being seedless and bearing few thorns; less dwarf and less thorny but with larger flowers than the Pixie, and more bushy with larger foliage and larger flowers than the Cinderella.

No references cited.